United States Patent
Fessi et al.

(10) Patent No.: US 9,910,027 B2
(45) Date of Patent: Mar. 6, 2018

(54) DIAGNOSTIC METHOD

(71) Applicant: Conopco, Inc., Englewood Cliffs, NJ (US)

(72) Inventors: Myriam Fessi, Liverpool (GB); Alexander James Margetts, Marlborough (GB); Stephen Lee Wire, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 119 days.

(21) Appl. No.: 14/889,462

(22) PCT Filed: May 7, 2014

(86) PCT No.: PCT/EP2014/059388
§ 371 (c)(1),
(2) Date: Nov. 6, 2015

(87) PCT Pub. No.: WO2014/184077
PCT Pub. Date: Nov. 20, 2014

(65) Prior Publication Data
US 2016/0195511 A1 Jul. 7, 2016

(30) Foreign Application Priority Data
May 13, 2013 (EP) .................................. 13167491

(51) Int. Cl.
*G01N 33/483* (2006.01)
*G01N 21/88* (2006.01)
*G01N 21/84* (2006.01)

(52) U.S. Cl.
CPC ..... *G01N 33/4833* (2013.01); *G01N 21/8803* (2013.01); *G01N 2021/8444* (2013.01)

(58) Field of Classification Search
CPC .................................................. G01N 33/4833
See application file for complete search history.

(56) References Cited

U.S. PATENT DOCUMENTS

| | | | | |
|---|---|---|---|---|
| 5,461,925 A | * | 10/1995 | Nguyen | G01N 3/08 73/160 |
| 5,694,953 A | * | 12/1997 | Stephan | A45D 19/00 132/160 |
| 7,261,000 B2 | | 8/2007 | Sherman et al. | |
| 2005/0238793 A1 | * | 10/2005 | Sherman | A61K 8/00 427/8 |

FOREIGN PATENT DOCUMENTS

| | | |
|---|---|---|
| CN | 1947010 | 4/2007 |
| JP | 2003040727 | 2/2003 |
| KR | 20080067433 | 7/2008 |

OTHER PUBLICATIONS

Search Report in EP13167491 dated Nov. 7, 2013. pp. 1 to 2.
Search Report in PCTEP2014059388 dated Jun. 3, 2014. pp. 3 to 6.
(Continued)

*Primary Examiner* — Manish S Shah
*Assistant Examiner* — Timothy Graves
(74) *Attorney, Agent, or Firm* — Karen E. Klumas

(57) ABSTRACT

Method and device for assessing the physical state of a hair fiber by crossing a single hair fiber and comparing a physical attribute of each part of the same fiber.

5 Claims, 2 Drawing Sheets

(56) References Cited

OTHER PUBLICATIONS

"Byzantine Boxwood Double-Sided Comb", Timeline Auctions, Jun. 23, 2011, XP055087021. pp. 7 to 7.
Written Opinion in EP13167491 dated Nov. 7, 2013. pp. 8 to 11.
Written Opinion in PCTEP2014059388 dated Jun. 3, 2014. pp. 12 to 18.
Zhan et al., SEM Observation of Head-Hair from Healthy Chinese, ACTA Anatomyca Sinica, 1983, pp. 334-337 vol. 14—No. 3 (with human English Translation).

* cited by examiner

DIAGNOSTIC METHOD

The present invention relates to a method for assessing the physical state of hair fibres.

The prior art discloses various ways of measuring the damage of hair.

US 2005/238793 A1 discloses a method of assessing damage of a fibrous substrate comprises the steps of: (a) providing said fibrous substrate having a length, a root end, and a tip end; (b) providing a means for assessing substrate moisture content; (c) using said means for assessing substrate moisture content to obtain at least a first measured moisture content value for said fibrous substrate at a first position along the length of said fibrous substrate and a second measured moisture content value for said fibrous substrate at a second position along the length of said fibrous substrate; (d) comparing said measured moisture content values with each other to obtain a measured moisture content differential; and (e) correlating said measured moisture content differential to a substrate damage value for said fibrous substrate.

KR 2008 0067433 A discloses a system and a method for measuring damaged hair by performing objective measurement by converting an image of hair into data to compare the data with reference data of healthy hair. The system measuring damaged hair includes a hair magnifying and photographing unit, a display unit, a numerical operation unit, a comparative analysis unit, and an output unit.

Methods for measuring the physical state of hair fibres by physically handling the hair or visualising individual fibres under high magnification are also known.

Despite the prior art we have found that there is a need for improved methods for rapidly assessing the physical state of hair fibres.

Accordingly, and in a first aspect, the present invention provides a method for assessing the physical state of a hair fibre by crossing a single hair fibre and comparing a physical attribute of each part of the same fibre.

Preferably, the comparison is made between the parts of the hair fibre substantially where the fibre crosses itself. This allows the user to make a quick and accurate assessment as to the hair's general state.

Preferably, the comparison is made within 10, more preferably within 5 hair widths of the crossing, based on the part of the fibre with the greatest width.

Preferably, the hair fibre crosses itself within a 'root region', which is less than 50% the length of the fibre from a root end, more preferably within 50 mm from the root end, and a 'tip region', which is more than 50% the length of the hair fibre from the root end, preferably within 50 mm from the tip of the hair fibre.

Preferably, the physical attribute is selected from colour, width, shine and transparency.

This permits the assessor to assess how the physical integrity of the hair fibre has been depleted along its length. Typically, a hair fibre will lose its outer coating of cuticle and so will degrade along its length over time. The rate that it does this will be dependent on genetic predisposition as well as any treatments or environmental conditions the fibre has been subjected to. For example, a hair fibre which has received multiple chemical treatments will be more damaged than one which has not received any treatments. Such a hair fibre will lose its physical integrity faster than a hair fibre which is not so treated.

Accordingly, the assessor is not measuring the fact that degradation has occurred but instead the rate of degradation. This rate of degradation is a more useful assessment of the health of the hair than conventional assessments.

Preferably, the assessor places the root or the tip of the hair fibre at a predetermined point so that the conclusion made for that hair fibre can be compared with a conclusion made for another hair fibre.

More preferably, the conclusion for a hair fibre may be compared to a hair fibre of the same consumer but after a period of differing quotidian hair treatment regime such that an assessment of the impact of the new regime can be made.

The new regime may be the use of a different hair treatment composition.

This is considered to be a better measure of the state of the hair than a general assessment made of many hair fibres simultaneously.

Where the hair fibre parts cross two angles are created. Preferably, the smaller of the vertical angles between the hair fibre parts at the point of crossing is from 30 to 90 degrees.

Preferably, the method comprises a recommendation to the consumer to use a particular product based on the conclusion as to the physical state of the hair fibres.

In a second aspect there is provided a device for maintaining a hair fibre such that a direct comparison between different parts of the same hair fibre may be made.

Preferably, such a device comprises a comparison plate which comprises a first and second pair of opposing notches.

Preferably the comparison plate comprises a focus area where an imaginary line drawn between each pair of opposing notches meet.

Preferably, the comparison plate is substantially circular, substantially oval, substantially rectangular or substantially square. Most preferably, it is substantially circular.

Preferably, the comparison plate comprises a means for co-operating with an imaging device to facilitate assessment. Such an imaging device might be a microscope.

Preferably, the device comprises a handle. Preferably, the handle is substantially within the same plane as the comparison plate. More preferably, the handle extends away from the comparison plate.

Preferably, the device comprises a wrap section where a hair fibre may be wrapped around until sufficient length has been exhausted such that a predetermined section of the fibre may be compared. Preferably, the handle comprises a wrap section.

Preferably, a line drawn between each pair of opposing notches has a smallest angle of from 30 to 90 degrees.

Embodiments of the invention will now be described with reference to the following non-limiting drawings in which.

Figure 1:
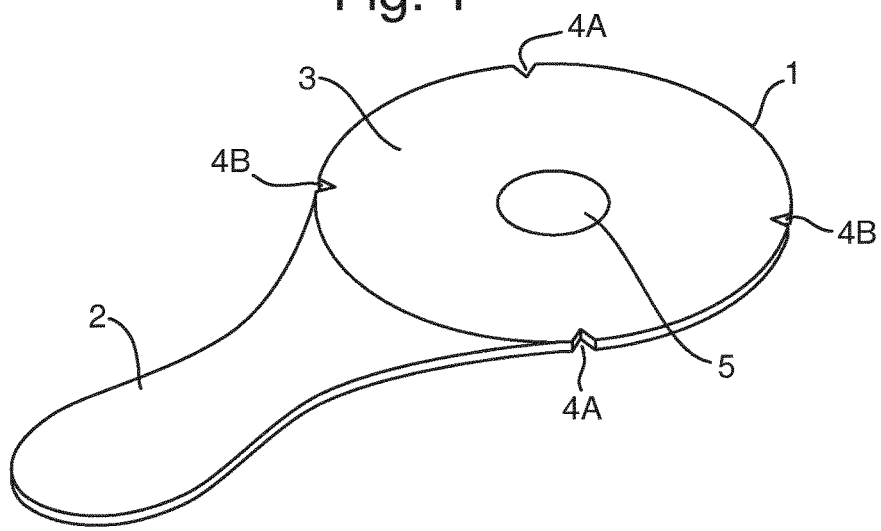
FIG. 1 is a perspective of a device according to claim 8.

In detail, FIG. 1 shows a device (1) with a handle (2) and a flat plate (3). The flat plate (3) has a focus area (5) where two parts of the same hair fibre are crossed and compared.

The plate (3) has a pair of opposing notches (4A and 4B) for receiving a hair fibre.

Figure 2:
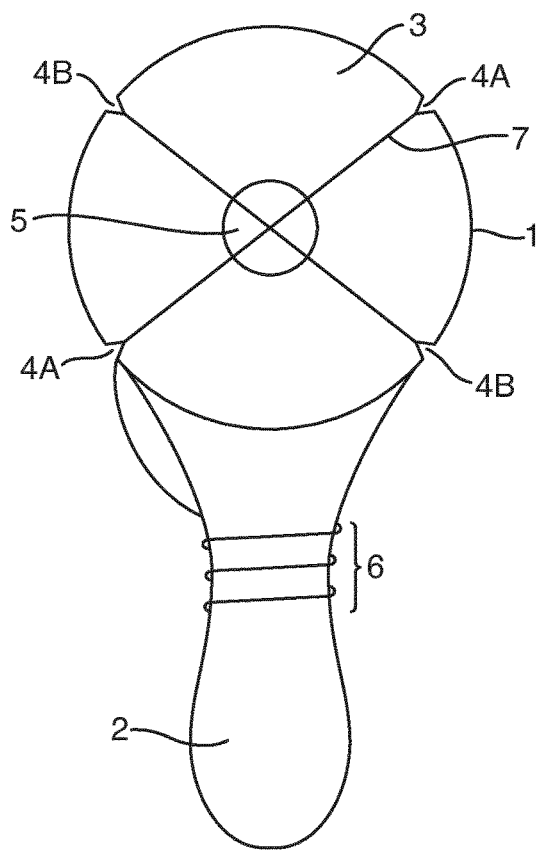
FIG. 2 is a plan of the same device in use.

FIG. 2 shows the same device but with a hair fibre (7) maintained by the pair of opposing notches (4A and 4B). The distal end of the hair fibre is wound around the top part (6) of the handle (2).

Figure 3:
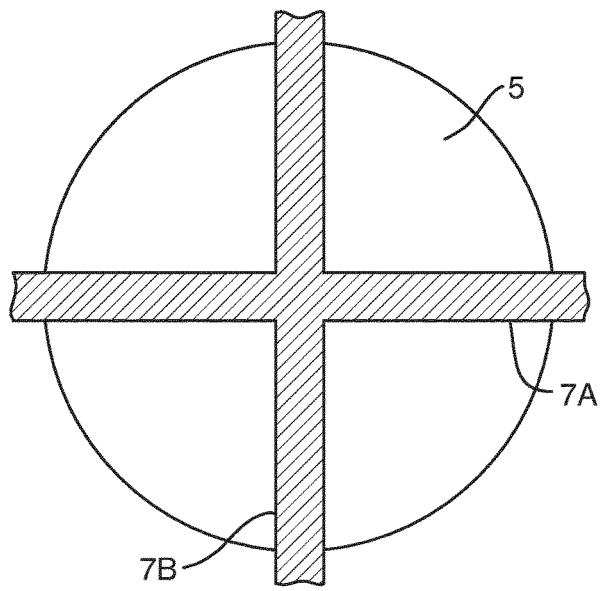
FIG. 3 is a close-up plan of the focus area of the same device in use.

FIG. 3 shows the focus area (5) with the two different parts of the same hair fibre (7A and 7B) crossed to facilitate comparison between different parts of the same fibre.

Figure 4:
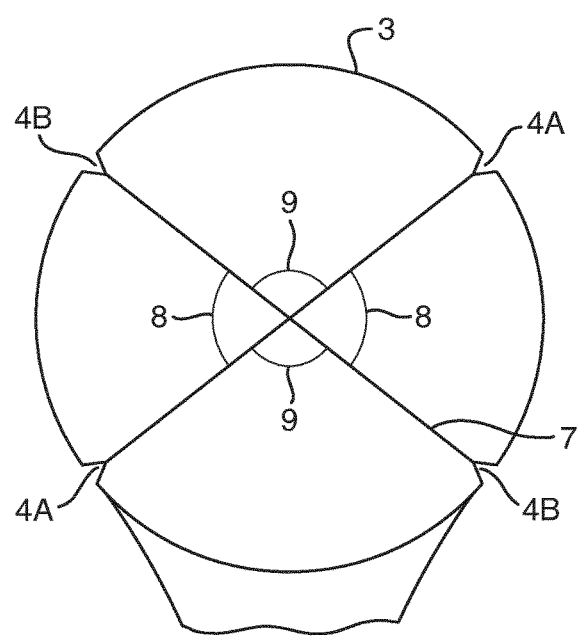

FIG. 4 shows a plan of the viewing plate (3) with a hair fibre (7) crossed in the centre. Two angles are created by the crossed hair a smaller vertical angle (8) and a larger vertical angle (9).

The invention claimed is:

1. Method for assessing the physical state of a hair fibre comprising:

placing a single hair fibre, the hair fibre having a root end and a tip end, on a flat viewing plate having a first pair of opposing notches and a second pair of opposing notches, the first and second pair of notches being positioned such that a first imaginary line drawn between the first pair of opposing notches intersects with a second imaginary line drawn between the second pair of opposing notches in what is a focus area of the viewing plate, wherein the smallest angle formed by the intersecting first imaginary line and second imaginary line is between 30 and 90 degrees, with the hair fibre being placed on the viewing plate between the first pair of notches and the second pair of notches such that the hair fibre crosses over itself within the focus area of the viewing plate; and comparing the hair fibre substantially where the fibre crosses itself for colour, width, shine and/or transparency.

2. Method according to claim 1, whereby the hair fibre is crossed within a 'root region', which is less than 50% the length of the fibre from a root end, and a 'tip region', which is more than 50% the length of the hair fibre from the root end.

3. Method for recommending a product to a consumer by determining the condition of the hair by a method according to claim 1 and then identifying a product from a range of products.

4. A device for evaluating the condition of a hair fibre, the device comprising: a substantially circular flat viewing plate having a first pair of opposing notches and a second pair of opposing notches, the first and second pair of notches being positioned such that a first imaginary line drawn between the first pair of opposing notches intersects with a second imaginary line drawn between the second pair of opposing notches in a focus area of the viewing plate, wherein the smallest angle formed by the intersecting first imaginary line and second imaginary line is between 30 and 90 degrees.

5. The device according to claim 4, on which a hair fibre has been placed such that a first portion of the hair fibre is maintained between the first pair of notches along the first imaginary line and a second portion of the hair fibre is maintained between the second pair of notches along the second imaginary line such that the hair fibre is crossed over itself within the focus area of the viewing plate.

* * * * *